US012791411B2

(12) United States Patent
Fukui

(10) Patent No.: US 12,791,411 B2
(45) Date of Patent: Nov. 10, 2026

(54) APPARATUS, SYSTEM AND METHOD TO DEDUCE A FORCE APPLIED TO A TARGET OBJECT BASED ON PRESSURE DATA AND CHARACTERISTIC HAND DATA

(71) Applicant: Mitsubishi Electric Corporation, Tokyo (JP)

(72) Inventor: Kotaro Fukui, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 396 days.

(21) Appl. No.: 18/367,511

(22) Filed: Sep. 13, 2023

(65) Prior Publication Data

US 2024/0003766 A1 Jan. 4, 2024

Related U.S. Application Data

(63) Continuation of application No. PCT/JP2021/015283, filed on Apr. 13, 2021.

(51) Int. Cl.

*G01L 5/16* (2020.01)
*A61B 5/00* (2006.01)
*G01L 5/00* (2006.01)

(52) U.S. Cl.

CPC .............. *G01L 5/16* (2013.01); *A61B 5/6806* (2013.01); *G01L 5/0028* (2013.01); *A61B 2503/20* (2013.01); *A61B 2562/0247* (2013.01)

(58) Field of Classification Search

CPC .............. A61B 5/6806; A61B 2503/20; A61B 2562/0247; G01L 5/16; G01L 5/0028

See application file for complete search history.

(56) References Cited

U.S. PATENT DOCUMENTS 6,694,194 B2 2/2004 Oda et al.
11,325,029 B2 5/2022 Nakamura
(Continued)

FOREIGN PATENT DOCUMENTS

CN 106445168 A 2/2017
CN 110262664 A 9/2019
(Continued)

OTHER PUBLICATIONS

German Office Action for German Application No. 11 2021 007 040.1, dated Jun. 11, 2024, with English translation.
(Continued)

*Primary Examiner* — Xuan M Thai
*Assistant Examiner* — Shauna-Kay Hall
(74) *Attorney, Agent, or Firm* — Birch, Stewart, Kolasch & Birch, LLP

(57) ABSTRACT

A contact information obtaining apparatus includes an applied-pressure direction deducing unit, a reaction calculation unit, and a determination unit. The applied-pressure direction deducing unit uses pressure data directed to pressure that a worker is applying to a target object by a hand of the worker, direction data directed to a direction concerning the hand measured and characteristic data that indicates a characteristic of the hand, to deduce an applied-pressure direction of the pressure that the hand is applying to the target object and a direction relative to the target object. The reaction calculation unit uses the pressure data and the deduced applied-pressure direction to calculate an applied-pressure reaction that is a reaction of the target object to the hand applying force to the target object. The determination unit determines whether or not the applied-pressure reaction is within a reference range.

8 Claims, 7 Drawing Sheets

(56) References Cited

U.S. PATENT DOCUMENTS

| | | | | |
|---|---|---|---|---|
| 2002/0049510 | A1 | 4/2002 | Oda et al. | |
| 2010/0245237 | A1 | 9/2010 | Nakamura | |
| 2016/0018278 | A1* | 1/2016 | Jeter | G16H 40/63 340/665 |
| 2017/0052074 | A1* | 2/2017 | Watazu | G06F 3/00 |
| 2017/0235364 | A1 | 8/2017 | Nakamura et al. | |
| 2019/0290202 | A1 | 9/2019 | Di Pardo et al. | |
| 2019/0357811 | A1* | 11/2019 | Di Pardo | A61B 5/1125 |
| 2020/0117271 | A1 | 4/2020 | Bosworth et al. | |
| 2020/0126447 | A1* | 4/2020 | Yoshimoto | G01D 7/08 |
| 2020/0201433 | A1 | 6/2020 | Emokpae | |
| 2020/0209966 | A1 | 7/2020 | Nakamura et al. | |
| 2020/0246692 | A1 | 8/2020 | Nakagawa et al. | |
| 2021/0056646 | A1* | 2/2021 | Yoshimoto | G06F 3/014 |
| 2022/0207978 | A1* | 6/2022 | Ishimaru | A41D 19/015 |

FOREIGN PATENT DOCUMENTS

| | | | |
|---|---|---|---|
| GB | 2467461 | A | 8/2010 |
| JP | 2000-311047 | A | 11/2000 |
| JP | 2001-133300 | A | 5/2001 |
| JP | 2002-132487 | A | 5/2002 |
| JP | 2006-58973 | A | 3/2006 |
| JP | 2008-33603 | A | 2/2008 |
| JP | 2009-236602 | A | 10/2009 |
| JP | 2010-221359 | A | 10/2010 |
| JP | 2011-179885 | A | 9/2011 |
| JP | 2012-73830 | A | 4/2012 |
| JP | 2017-97438 | A | 6/2017 |
| JP | 2016-14954 | A | 1/2018 |
| JP | 2018-173863 | A | 11/2018 |
| JP | 2018-181185 | A | 11/2018 |
| JP | 2019-32239 | A | 2/2019 |
| JP | 2019-128940 | A | 8/2019 |
| JP | 2019-160035 | A | 9/2019 |
| JP | 2019-204310 | A | 11/2019 |
| JP | 2019-215711 | A | 12/2019 |
| JP | 2020-61184 | A | 4/2020 |
| JP | 2020-64429 | A | 4/2020 |
| JP | 2020-91904 | A | 6/2020 |
| JP | 6822715 | B1 | 1/2021 |
| WO | WO 2019/077652 | A1 | 4/2019 |

OTHER PUBLICATIONS

International Search Report for International Application No. PCT/JP2022/020458, dated Aug. 2, 2022, with an English translation.

International Search Report (PCT/ISA/210), issued in PCT/JP2021/015283, dated May 18, 2021.

Indian Office Action for Indian Application No. 202447080092, dated Jul. 21, 2026, with English translation.

* cited by examiner

APPARATUS, SYSTEM AND METHOD TO DEDUCE A FORCE APPLIED TO A TARGET OBJECT BASED ON PRESSURE DATA AND CHARACTERISTIC HAND DATA

CROSS REFERENCE TO RELATED APPLICATIONS

This application is a Continuation of PCT International Application No. PCT/JP2021/015283, filed on Apr. 13, 2021, which is hereby expressly incorporated by reference into the present application.

TECHNICAL FIELD

The present disclosure relates to a contact information obtaining apparatus, a contact information obtaining system, a contact information obtaining method, and a contact information obtaining program.

BACKGROUND ART

Since there is a case where a tactile examination is used in an inspection of a machine and a device, technology to make the tactile examination remote is in demand. A main purpose of the tactile examination is to verify how firmly fastened target equipment is and to verify that the target equipment operates smoothly. Since there is a wide variety of target equipment for the tactile examination and work spaces at sites where the tactile examination is executed are often limited, a system that obtains information from a sense of touch of a worker without using a large-scale device at a time of making the tactile examination remote is necessary.

Patent Literature 1 discloses technology that deduces pressure that a finger applies to a target object by measuring force put on a gate shaped member covering a side surface of the finger and applying a measured result to a deducing model concerning the finger. In the present technology, the deducing model is switched depending on whether or not there is movement of a fingertip.

CITATION LIST

Patent Literature

Patent Literature 1: JP 2019-032239 A

SUMMARY OF INVENTION

Technical Problem

According to the technology disclosed in Patent Literature 1, since the force applied to the target object is deduced without taking an orientation of a pressure sensor that measures pressure that the finger applies to the target object and a characteristic of a hand of a worker into consideration, there is an issue where accuracy in deducing a reaction of the target object is low in a tactile examination.

The present disclosure aims to deduce force applied to a target object by taking an orientation of a pressure sensor that measures pressure that a finger applies to a target object and a characteristic of a hand of a worker into consideration.

Solution to Problem

A contact information obtaining apparatus according to the present disclosure includes:

an applied-pressure direction deducing unit, using pressure data that a pressure sensor that measures pressure that a worker is applying to a target object by a hand of the worker measured, direction data that a direction sensor that measures a direction concerning the hand measured, and characteristic data that indicates a characteristic of the hand, to deduce an applied-pressure direction that is a direction of the pressure that the hand is applying to the target object and a direction relative to the target object;

a reaction calculation unit, using the pressure data and the applied-pressure direction that is deduced, to calculate an applied-pressure reaction that is a reaction of the target object to the hand applying force to the target object; and a determination unit to determine whether or not the applied-pressure reaction is within a reference range.

Advantageous Effects of Invention

According to the present disclosure, an applied-pressure direction is deduced using direction data and characteristic data. Consequently, according to the present disclosure, force applied to a target object can be deduced by taking an orientation of a pressure sensor that measures pressure that a finger applies to the target object and a characteristic of a hand of a worker into consideration.

DESCRIPTION OF EMBODIMENTS

Figure 1:
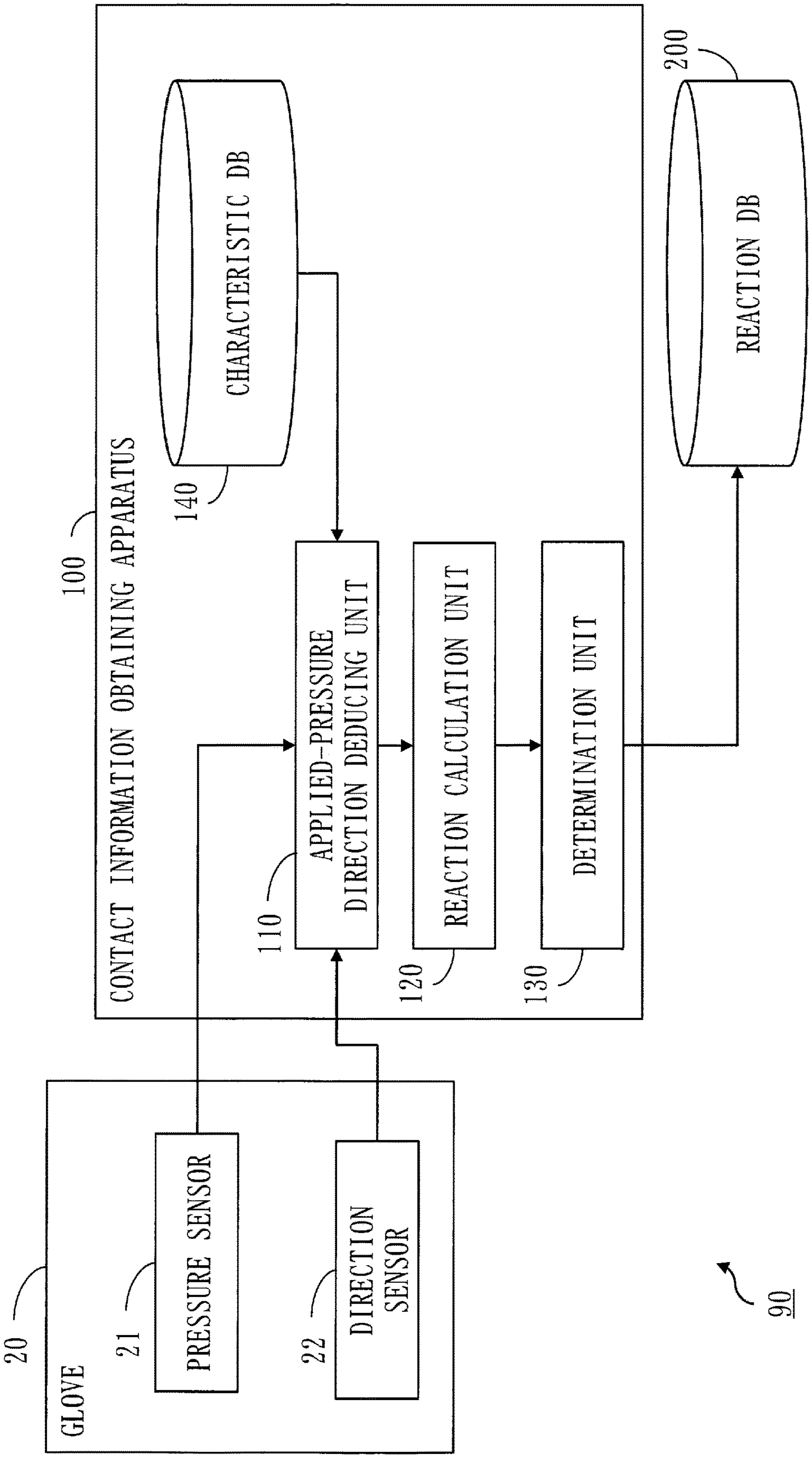
FIG. 1 is a diagram illustrating an example of a configuration of a contact information obtaining system 90 according to Embodiment 1.

In the description of the embodiment and in the drawings, the same reference signs are added to the same elements and corresponding elements. Descriptions of elements having the same reference signs added will be suitably omitted or simplified. Arrows in the drawings mainly indicate flows of data or flows of processes. “Unit” may be suitably replaced with “circuit”, “step”, “procedure”, “process”, or “circuitry”.

Embodiment 1

The present embodiment will be described in detail below by referring to the drawings.

*Description of Configuration*

FIG. 1 illustrates an example of a configuration of a contact information obtaining system 90 according to the present embodiment. The contact information obtaining system 90, as illustrated in the present diagram, includes a glove 20, a contact information obtaining apparatus 100, and a reaction DB (Database) 200. The contact information obtaining apparatus 100 and the reaction DB 200 may be integrally configured.

The glove 20 is a glove that a worker wears at a time of executing a tactile examination. A pressure sensor 21 and a direction sensor 22 are attached to the glove 20. Any number of each of the pressure sensor 21 and the direction sensor 22 may be attached to the glove 20. The worker may wear the glove 20 on one hand or may wear the glove 20 on both hands.

The tactile examination, as a specific example, is to shake a target object 300, turn a pulley that is the target object 300, measure force put on a rope that is the target object 300, push or pull on the rope that is the target object 300, verify whether or not a connector that is the target object 300 is appropriately inserted, verify whether or not the target object 300 moves smoothly, verify in a time series how pressure is put on the target object 300 by moving a position of the target object 300 to detect the target object 300 being caught and the like, or to verify by pressing a switch that is the target object 300, whether or not the switch can be pressed smoothly. Here, the target object 300 is a target of the tactile examination, and there may be a plurality of target objects 300 of a type or there may be target objects 300 of a plurality of types.

The pressure sensor 21 is a sensor that measures pressure that the worker is applying to the target object 300 using the hand of the worker. The worker may exist in a plurality of numbers. The pressure sensor 21 is suitably attached to a part where a portion of a hand used at a time of the worker executing the tactile examination touches. The pressure sensors 21, as specific examples, are attached to the glove 20 on a part that touches a pad of each finger of the hand of the worker and on a part that touches a palm of the worker. The finger, unless otherwise noted, means the finger of the hand. The pressure sensor 21 may measure pressure that each finger of at least one finger of the hand of the worker is applying to the target object 300.

The direction sensor 22 is a sensor that measures a direction concerning the hand and is a sensor to measure a direction of the pressure sensor 21, and typically consists of an azimuth sensor and an acceleration sensor. The direction concerning the hand, as a specific example, is a direction of the finger or a direction of the palm. The direction, as a specific example, consists of an azimuth and an inclination from a horizontal slope. A coordinate system that specifies a direction may be defined in any manner. The direction sensors 22, as specific examples, are attached to a part that touches a dorsal side of each finger of the hand and that is opposite the part that the pressure sensor 21 is attached and to a part that touches a dorsal side of the palm of the worker. The direction sensor 22 may measure a direction of each finger of at least one finger of the hand of the worker.

The contact information obtaining apparatus 100 includes an applied-pressure direction deducing unit 110, a reaction calculation unit 120, a determination unit 130, and a characteristic DB 140.

The applied-pressure direction deducing unit 110, using pressure data that the pressure sensor 21 measured, direction data that the direction sensor 22 measured, and characteristic data that indicates a characteristic of the hand, deduces an applied-pressure direction. The applied-pressure direction is a direction of the pressure that the hand of the worker is applying to the target object 300, and is a direction relative to the target object 300. The applied-pressure direction deducing unit 110 may deduce a plurality of applied-pressure directions in a case where the worker is applying pressure to the target object 300 using a plurality of fingers.

The reaction calculation unit 120, using the pressure data and the applied-pressure direction that is deduced, calculates an applied-pressure reaction that is a reaction of the target object 300 caused by the worker applying pressure to the target object 300. The applied-pressure reaction, as a specific example, is at least one of excitation force on the target object 300 and a response of the target object 300.

The determination unit 130 determines whether or not the applied-pressure reaction is within a reference range. The reference range is a range of the applied-pressure reaction that must be satisfied in the tactile examination on the target object 300 and a range of the applied-pressure reaction that is quantified.

The characteristic DB 140 stores as the characteristic data, data that indicates a shape and an elasticity value of each finger of at least one finger of a hand of each worker. The shape of each finger, as specific examples, is a length and a thickness of each finger. Taking the elasticity value of each finger of each worker not always being constant, as a specific example, the elasticity value differs for each season into consideration, a plurality of types of elasticity values for each finger of each worker may be stored. The characteristic DB 140 may store a shape and an elasticity value of a different portion of the hand of each worker.

The reaction DB 200 stores data that indicates the applied-pressure reaction in the tactile examination on each target object 300. An information presentation device that is possible to reproduce sense of force information, vibration, or the like as physical motion may reproduce the tactile examination on each target object 300 using the data that the reaction DB 200 has stored. The information presentation device is a device that reproduces the applied-pressure reaction that the reaction calculation unit 120 calculated, and as a specific example, is a haptic device.

Figure 2:
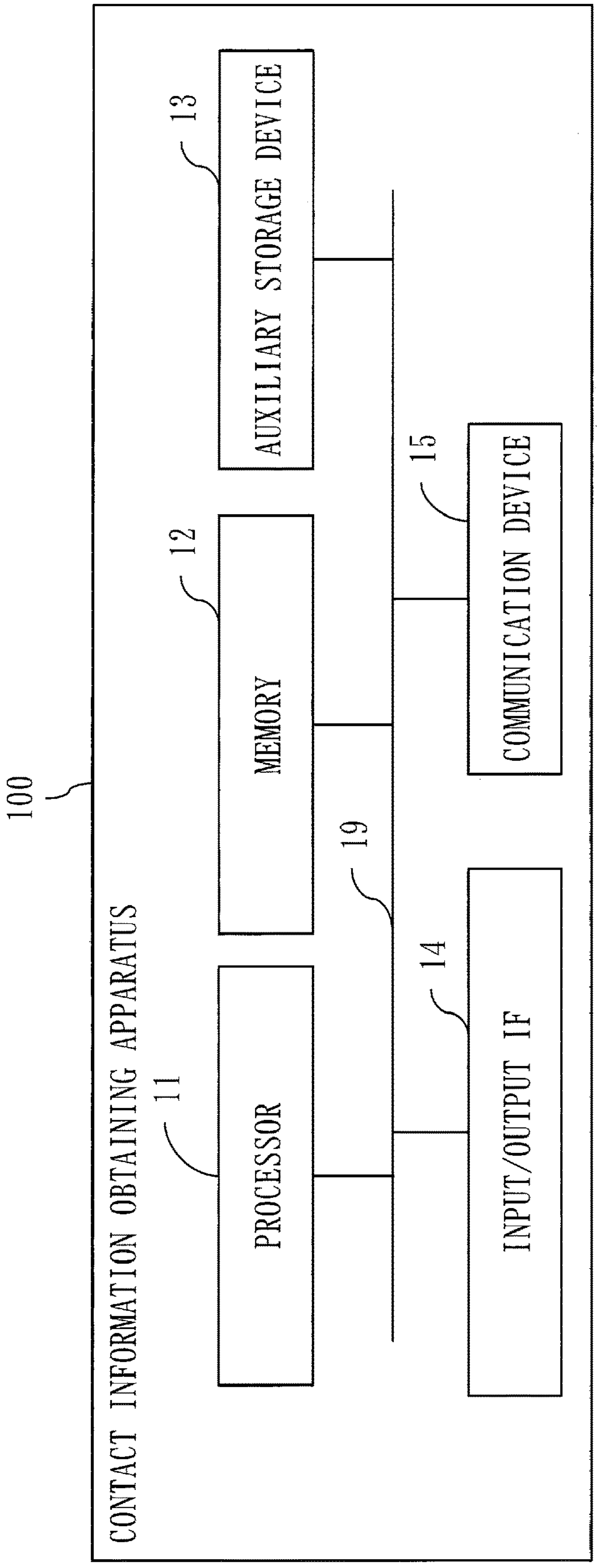
FIG. 2 is a diagram illustrating an example of a hardware configuration of a contact information obtaining apparatus 100 according to Embodiment 1.

FIG. 2 illustrates an example of a hardware configuration of the contact information obtaining apparatus 100 according to the present embodiment. The contact information obtaining apparatus 100 consists of a computer. The contact information obtaining apparatus 100 may consist of a plurality of computers.

The contact information obtaining apparatus 100, as illustrated in the present diagram, is a computer that includes hardware such as a processor 11, a memory 12, an auxiliary storage device 13, input/output IF (Interface) 14, a communication device 15, and the like. These pieces of hardware are suitably connected through a signal line 19.

The processor 11 is an IC (Integrated Circuit) that performs a calculation process, and controls hardware that the computer includes. The processor 11, as a specific example, is a CPU (Central Processing Unit), a DSP (Digital Signal Processor), or a GPU (Graphics Processing Unit).

The contact information obtaining apparatus 100 may include a plurality of processors that replace the processor 11. The plurality of processors share roles of the processor 11.

The memory 12 is typically a volatile storage device. The memory 12 is also called a main storage device or a main memory. The memory 12, as a specific example, is a RAM (Random Access Memory). Data stored in the memory 12 is saved in the auxiliary storage device 13 as necessary.

The auxiliary storage device 13 is typically a non-volatile storage device. The auxiliary storage device 13, as a specific example, is a ROM (Read Only Memory), an HDD (Hard Disk Drive), or a flash memory. Data stored in the auxiliary storage device 13 is loaded into the memory 12 as necessary.

The memory 12 and the auxiliary storage device 13 may be configured integrally.

The input/output IF 14 is a port to which an input device and an output device are connected. The input/output IF 14, as a specific example, is a USB (Universal Serial Bus) terminal. Input devices, as specific examples, are a keyboard and a mouse.

The output device, as a specific example, is a display.

The communication device 15 is a receiver and a transmitter. The communication device 15, as a specific example, is a communication chip or an NIC (Network Interface Card).

Each unit of the contact information obtaining apparatus 100 may suitably use the input/output IF 14 and the communication device 15 at a time of communicating with a different device and the like.

The auxiliary storage device 13 has stored a contact information obtaining program. The contact information obtaining program is a program that causes a computer to enable functions of each unit that the contact information obtaining apparatus 100 includes. The contact information obtaining program is loaded into the memory 12, and executed by the processor 11. The functions of each unit that the contact information obtaining apparatus 100 includes are enabled by software.

Data used at a time of executing the contact information obtaining program, data obtained by executing the contact information obtaining program, and the like are suitably stored in a storage device. Each unit of the contact information obtaining apparatus 100 suitably utilizes the storage device. The storage device, as a specific example, consists of at least one of the memory 12, the auxiliary storage device 13, a register in the processor 11, and a cache memory in the processor 11. There is a case where data and information have an equal meaning. The storage device may be a device that is independent of the computer.

Functions of the memory 12 and the auxiliary storage device 13 may be enabled by a different storage device.

The contact information obtaining program may be recorded in a computer-readable non-volatile recording medium. The non-volatile recording medium, as a specific example, is an optical disc or a flash memory. The contact information obtaining program may be provided as a program product.

*Description of Operation*

An operation procedure of the contact information obtaining apparatus 100 is equivalent to a contact information obtaining method. A program that enables operation of the contact information obtaining apparatus 100 is equivalent to the contact information obtaining program.

Figure 3:
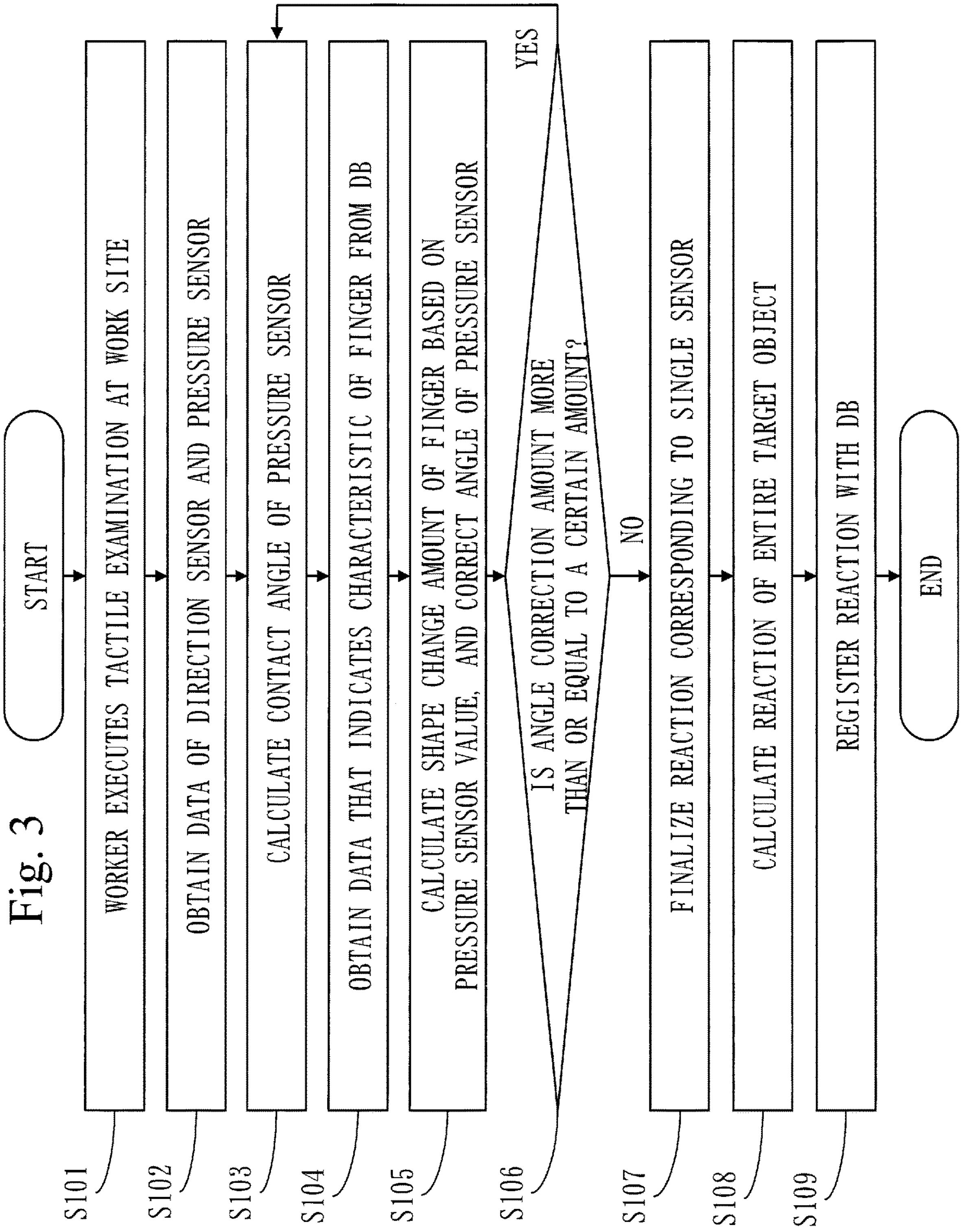
FIG. 3 is a flowchart illustrating operation of the contact information obtaining system 90 according to Embodiment 1.

FIG. 3 is a flowchart illustrating operation of the contact information obtaining system 90. The operation of the contact information obtaining system 90 will be described by referring to the present diagram.

(Step S101)

The worker wearing the glove 20 executes the tactile examination on the target object 300 at a work site, and the pressure sensor 21 and the direction sensor 22 collect data. The data that the pressure sensor 21 and the direction sensor 22 collected is suitably transmitted to the contact information obtaining apparatus 100.

Figure 4:
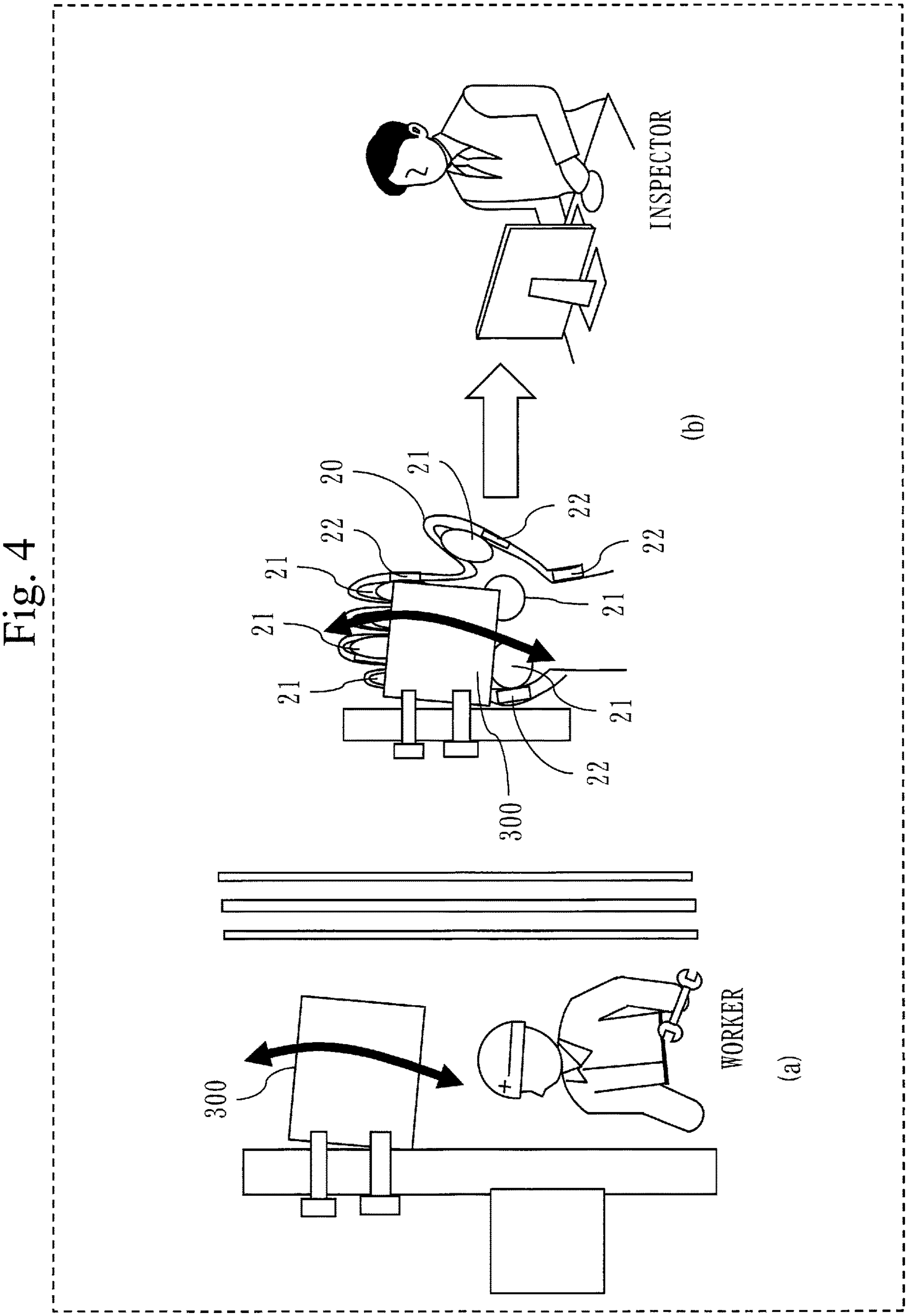
FIG. 4 is a diagram illustrating a tactile examination using the contact information obtaining system 90 according to Embodiment 1, (a) is a diagram illustrating a work site, and (b) is a diagram illustrating remotely verifying a situation of the tactile examination.

FIG. 4 illustrates the data that the pressure sensor 21 and the direction sensor 22 collected being transmitted to the contact information obtaining apparatus 100. Note that (a) of FIG. 4 illustrates the work site where the tactile examination is executed. Note that (b) of FIG. 4 illustrates the worker wearing the glove 20 shaking the target object 300 up and down and data that the pressure sensor 21 and the direction sensor 22 collected at this time being sent to the contact information obtaining apparatus 100 arranged remotely, and an inspector verifying a situation of the tactile examination remotely.

(Step S102)

The contact information obtaining apparatus 100 receives the data from the pressure sensor 21 and the direction sensor 22. The data that the contact information obtaining apparatus 100 receives may be raw data that each of the pressure sensor 21 and the direction sensor 22 obtained.

Below, the data that indicates pressure the pressure sensor 21 measured will be expressed as the pressure data, and the data that indicates a direction that the direction sensor 22 measured will be expressed as the direction data.

(Step S103)

The applied-pressure direction deducing unit 110 calculates a contact angle of the pressure sensor 21 with respect to the target object 300 based on the data received from the direction sensor 22.

(Step S104)

The applied-pressure direction deducing unit 110 locates as a work portion, each portion of the hand of the worker that the worker is using in the tactile examination based on the pressure data, and obtains from the characteristic DB 140, data that indicates a shape and an elasticity value of each work portion located. The work portion, as a specific example, is at least one of at least one of the fingers of the worker and the palm of the worker.

(Step S105)

The applied-pressure direction deducing unit 110 calculates a shape change amount of each work portion using the pressure data and the data on each work portion obtained from the characteristic DB 140, and corrects the contact angle calculated in step S103 based on each shape change amount calculated.

Here, an orientation of the pressure sensor 21 changes according to a shape change of the work portion. Furthermore, since there is a case where a misalignment also occurs between the orientation of the pressure sensor 21 and the applied-pressure direction, the applied-pressure direction deducing unit 110 deduces the applied-pressure direction using a deducing algorithm that deduces a shape change of the finger and a change in an orientation of force caused by the shape change of the finger. In a case where the work portion is a finger, when a sensor other than the pressure sensor 21 is provided on a side of the pad of the finger to deduce the shape change of the finger, workability in the tactile examination is lost. Therefore, in the present embodiment, the shape change of the finger is deduced by applying to the deducing algorithm, the data that the pressure sensor 21 measured without providing a sensor other than the pressure sensor 21 on the side of the pad of the finger, and the data that the characteristic DB 140 has stored.

Figure 5:
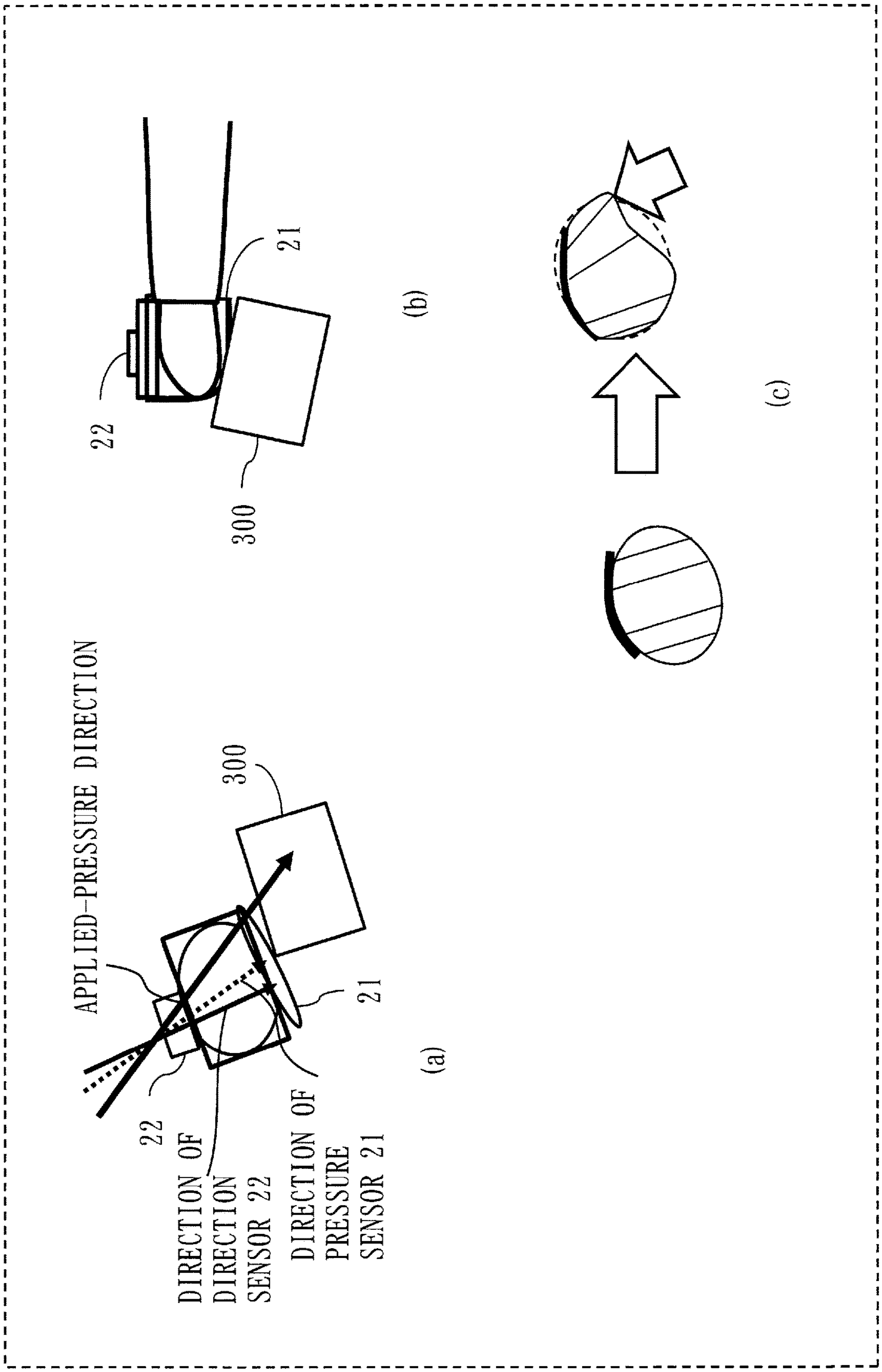
FIG. 5 is a diagram describing a shape change of a finger caused by applying pressure to a target object 300, (a) is a diagram describing an applied-pressure direction, (b) is a diagram illustrating the finger applying pressure to the target object 300, and (c) is a diagram illustrating the finger changing shape.

FIG. 5 is a diagram describing a shape change of a finger. Note that (a) of FIG. 5 illustrates a worker applying pressure to the target object 300 by a finger. In (a) of FIG. 5, in a case where the finger does not change shape, the orientation of the pressure sensor 21 and an orientation of the direction sensor 22 match, and the applied-pressure direction is an orientation that the direction sensor 22 indicates. The finger, however, changes shape by applied pressure, the orientation of the pressure sensor 21 changes according to the shape change of the finger, and as a result, the applied-pressure direction becomes as illustrated in (a) of FIG. 5. Here, the applied-pressure direction cannot be deduced accurately with only the direction sensor 22.

Note that (b) of FIG. 5 illustrates the worker applying pressure to the target object 300 using the finger.

Note that (c) of FIG. 5 illustrates the finger changing shape by the worker applying pressure to the target object 300 using the finger. Apart of the finger changes shape as illustrated on a right side by applying pressure to the target object 300.

(Step S106)

In a case where a correction amount of the contact angle in step S105 is more than or equal to a certain amount, the contact information obtaining apparatus 100 returns to step S103. In other cases, the contact information obtaining apparatus 100 proceeds to step S107.

(Step S107)

The reaction calculation unit 120 calculates magnitude and a direction of the applied-pressure reaction at each point of contact of the target object 300 corresponding to each piece of pressure data using the pressure data corresponding to each pressure sensor 21 and the applied-pressure direction that is deduced. The point of contact is a point at which the target object 300 and the pressure sensor 21 are in contact directly or indirectly.

(Step S108)

The reaction calculation unit 120 calculates an applied-pressure reaction of an entire the target object 300 using the magnitude and the direction of the applied-pressure reaction at each point of contact of the target object 300 calculated in step S107.

The determination unit 130 determines whether or not the applied-pressure reaction calculated is within the reference range, and suitably outputs a result that is determined.

(Step S109)

The reaction calculation unit 120 registers the applied-pressure reaction calculated in step S107 and step S108 with the reaction DB 200.

Description of Effect of Embodiment 1

As described above, according to the present embodiment, the applied-pressure reaction of the target object 300 can be deduced with relatively high accuracy while maintaining workability of the worker in the tactile examination relatively high.

*Other Configurations*

<Variation 1>

Figure 6:
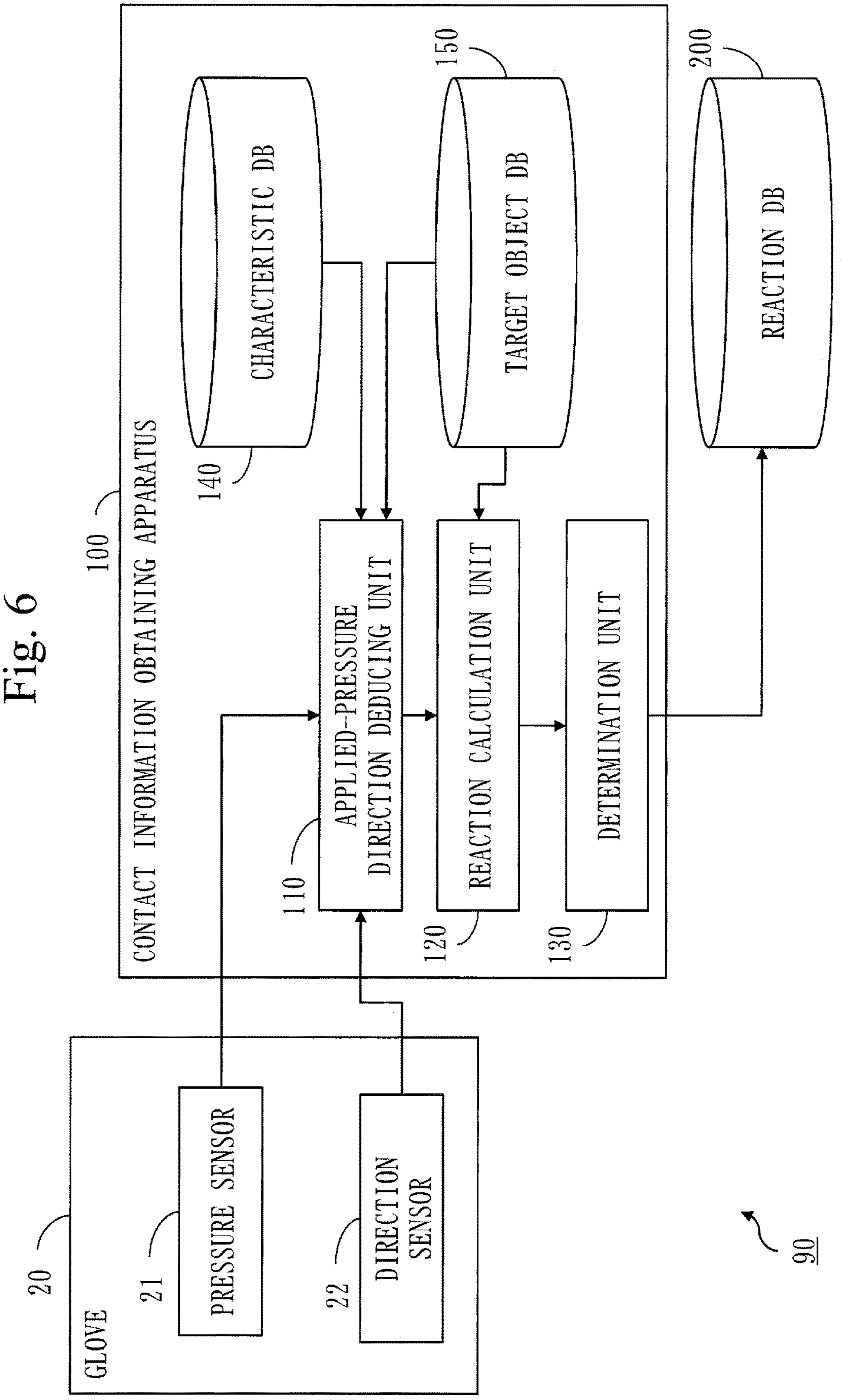
FIG. 6 is a diagram illustrating an example of a configuration of a contact information obtaining system 90 according to a variation of Embodiment 1.

FIG. 6 illustrates an example of a configuration of a contact information obtaining system 90 according to the present variation. As illustrated in the present diagram, the contact information obtaining apparatus 100 includes a target object DB 150.

The target object DB 150 stores target object data that indicates a three-dimensional shape and rigidity of each target object 300. The target object DB 150 may store only a three-dimensional shape and rigidity of a gripping part of each target object 300.

An applied-pressure direction deducing unit 110 according to the present variation deduces the applied-pressure direction using the target object data.

A reaction calculation unit 120 according to the present variation calculates the applied-pressure reaction using the target object data.

Below, a difference between operation of the contact information obtaining system 90 according to the present variation and the operation of the contact information obtaining system 90 according to Embodiment 1 will mainly be described.

(Step S104)

The applied-pressure direction deducing unit 110 also obtains together, data that the target object DB 150 has stored.

(Step S105)

The applied-pressure direction deducing unit 110 corrects the contact angle calculated in step S103 using also the data obtained from the target object DB 150. As a specific example, the applied-pressure direction deducing unit 110 deduces a gripping posture of the worker using the target object data obtained from the target object DB 150, and adjusts, based on the gripping posture deduced, the applied-pressure direction that is found based on the pressure data and the data obtained from the characteristic DB 140.

In step S107 and step S108, the reaction calculation unit 120 calculates the applied-pressure reaction using the target object data obtained from the target object DB 150. As a specific example, the reaction calculation unit 120 calculates a degree to which the applied-pressure reaction is realistically achieved based on the three-dimensional shape and the rigidity of the target object 300, and finds an applied-pressure reaction that has a high degree of realistically being achieved.

According to the present variation, since the applied-pressure direction is deduced by taking the three-dimensional shape and the rigidity of the target object 300 into consideration, accuracy in deducing the applied-pressure direction increase.

<Variation 2>

Figure 7:
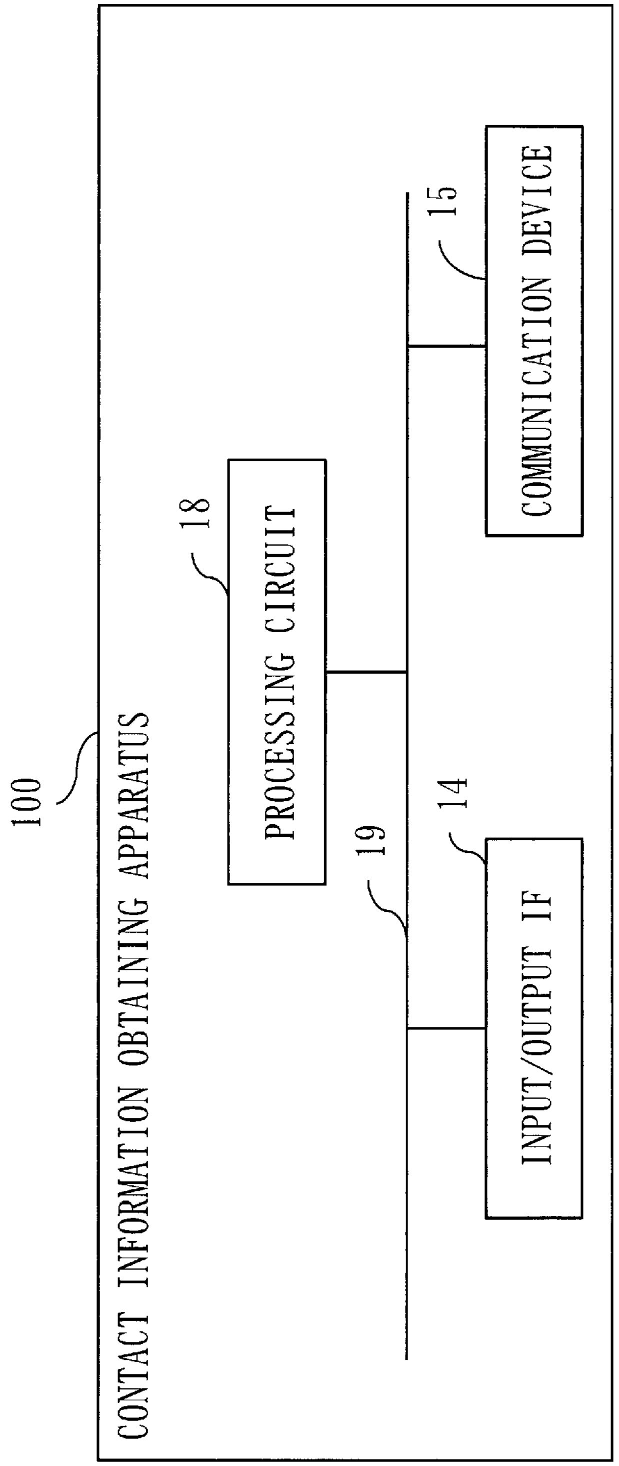
FIG. 7 is a diagram illustrating an example of a hardware configuration of a contact information obtaining apparatus 100 according to a variation of Embodiment 1.

FIG. 7 illustrates an example of a hardware configuration of a contact information obtaining apparatus 100 according to the present variation.

The contact information obtaining apparatus 100 includes a processing circuit 18 instead of the processor 11, the processor 11 and the memory 12, the processor 11 and the auxiliary storage device 13, or the processor 11, the memory 12, and the auxiliary storage device 13.

The processing circuit 18 is hardware that enables at least a part of each unit that the contact information obtaining apparatus 100 includes.

The processing circuit 18 may be dedicated hardware and may be a processor that executes a program stored in the memory 12.

In a case where the processing circuit 18 is dedicated hardware, the processing circuit 18, as a specific example, is a single circuit, a composite circuit, a programmed processor, a parallel programmed processor, an ASIC (ASIC is Application Specific Integrated Circuit), an FPGA (Field Programmable Gate Array), or a combination of these.

The contact information obtaining apparatus 100 may include a plurality of processing circuits that replace the processing circuit 18. The plurality of processing circuits share roles of the processing circuit 18.

In the contact information obtaining apparatus 100, a part of functions may be enabled by dedicated hardware and the rest of the functions may be enabled by software or firmware.

The processing circuit 18, as a specific example, is enabled by hardware, software, firmware, or a combination of these.

The processor 11, the memory 12, the auxiliary storage device 13, and the processing circuit 18 are generically called "processing circuitry". That is, functions of each functional element of the contact information obtaining apparatus 100 are enabled by the processing circuitry.

Other Embodiments

A description with regard to Embodiment 1 has been given, but within the present embodiment, a plurality of parts may be combined and executed. Or, the present embodiment may be executed partially. In addition, various changes may be made to the present embodiment as necessary, and the present embodiment may be arranged and executed in any manner, either fully or partially.

The embodiment mentioned above is an essentially preferred example, and is not intended to limit the present disclosure, the application of the present disclosure, and the scope of use. The procedures described using the flowchart and the like may be suitably changed.

REFERENCE SIGNS LIST

11: processor; 12: memory; 13: auxiliary storage device; 14: input/output IF; 15: communication device; 18: processing circuit; 19: signal line; 20: glove; 21: pressure sensor; 22: direction sensor; 90: contact information obtaining system; 100: contact information obtaining apparatus; 110: applied-pressure direction deducing unit; 120: reaction calculation unit; 130: determination unit; 140: characteristic DB; 150: target object DB; 200: reaction DB; 300: target object.

The invention claimed is:

1. A contact information obtaining apparatus comprising:

processing circuitry to:

using pressure data that a pressure sensor that measures pressure that a worker is applying to a target object by a hand of the worker measured, direction data that a direction sensor that measures a direction concerning the hand measured, and characteristic data that indicates a characteristic of the hand, deduce an applied-pressure direction that is a direction of the pressure that the hand is applying to the target object and a direction relative to the target object, using the pressure data and the applied-pressure direction that is deduced, calculate a magnitude and a direction of an applied-pressure reaction that is a reaction of the target object to the hand applying force to the target object, and determine whether or not the applied-pressure reaction is within a reference range, wherein the processing circuitry deduces the applied-pressure direction using target object data that indicates a three-dimensional shape and rigidity of the target object, and calculates the magnitude and the direction of the applied-pressure reaction using the three-dimensional shape and rigidity of the target object data.

2. The contact information obtaining apparatus according to claim 1, wherein the pressure sensor and the direction sensor are attached to a glove that the worker wears.

3. The contact information obtaining apparatus according to claim 1, wherein the pressure sensor measures pressure that each finger of at least one finger of the hand is applying to the target object, the direction sensor measures a direction of each finger of at least one finger of the hand, and the characteristic data includes data that indicates a shape and an elasticity value of each finger of at least one finger of the hand.

4. The contact information obtaining apparatus according to claim 1, wherein the direction sensor consists of an acceleration sensor and an azimuth sensor.

5. The contact information obtaining apparatus according to claim 1, wherein the applied-pressure reaction is at least one of excitation force on the target object and a response of the target object.

6. A contact information obtaining system comprising:

a device that reproduces the applied-pressure reaction that the processing circuitry according to claim 1 calculated.

7. A contact information obtaining method comprising:

deducing, using pressure data that a pressure sensor that measures pressure that a worker is applying to a target object by a hand of the worker measured, direction data that a direction sensor that measures a direction concerning the hand measured, and characteristic data that indicates a characteristic of the hand, an applied-pressure direction that is a direction of the pressure that the hand is applying to the target object and a direction relative to the target object;

calculating, using the pressure data and the applied-pressure direction that is deduced, a magnitude and a direction of an applied-pressure reaction that is a reaction of the target object to the hand applying force to the target object;

determining whether or not the applied-pressure reaction is within a reference range;

deducing the applied-pressure direction using target object data that indicates a three-dimensional shape and rigidity of the target object; and calculating the magnitude and the direction of the applied-pressure reaction using the three-dimensional shape and rigidity of the target object data.

8. A non-transitory computer readable medium storing a contact information obtaining program that causes a contact information obtaining apparatus that is a computer to execute:

an applied-pressure direction deducing process, using pressure data that a pressure sensor that measures pressure that a worker is applying to a target object by a hand of the worker measured, direction data that a direction sensor that measures a direction concerning the hand measured, and characteristic data that indicates a characteristic of the hand, to deduce an applied-pressure direction that is a direction of the pressure that the hand is applying to the target object and a direction relative to the target object;

a reaction calculation process, using the pressure data and the applied-pressure direction that is deduced, to calculate a magnitude and a direction of an applied-pressure reaction that is a reaction of the target object to the hand applying force to the target object; and a determination process to determine whether or not the applied-pressure reaction is within a reference range, wherein in the applied-pressure direction deducing process, the applied-pressure direction is deduced using target object data that indicates a three-dimensional shape and rigidity of the target object, and in the reaction calculation process, the magnitude and the direction of the applied-pressure reaction is calculated using the three-dimensional shape and rigidity of the target object data.

* * * * *